(12) United States Patent
Shuros et al.

(10) Patent No.: US 10,960,216 B2
(45) Date of Patent: Mar. 30, 2021

(54) EXTRACTION DEVICES CONFIGUED TO EXTRACT CHRONICALLY IMPLANTED MEDICAL DEVICES

(71) Applicant: CARDIAC PACEMAKERS, INC., St. Paul, MN (US)

(72) Inventors: Allan Charles Shuros, St. Paul, MN (US); Brian Soltis, St. Paul, MN (US); Arjun D. Sharma, St Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 389 days.

(21) Appl. No.: 15/474,982

(22) Filed: Mar. 30, 2017

(65) Prior Publication Data

US 2017/0281952 A1    Oct. 5, 2017

Related U.S. Application Data

(60) Provisional application No. 62/316,074, filed on Mar. 31, 2016.

(51) Int. Cl.
*A61N 1/375*    (2006.01)
*A61N 1/372*    (2006.01)
(Continued)

(52) U.S. Cl.
CPC ........ *A61N 1/3756* (2013.01); *A61B 17/3209* (2013.01); *A61B 17/320016* (2013.01);
(Continued)

(58) Field of Classification Search
CPC ...... A61B 17/320016; A61B 17/32056; A61B 17/3209; A61B 17/3468;
(Continued)

(56) References Cited

U.S. PATENT DOCUMENTS 5,318,564 A * 6/1994 Eggers ............... A61B 18/1233
606/47
5,810,810 A * 9/1998 Tay ..................... A61B 17/0057
606/50
(Continued)

FOREIGN PATENT DOCUMENTS

JP       5480372 A    11/2012
JP    2015507970 A     3/2015
(Continued)

OTHER PUBLICATIONS

Bongiorni et al., "Retrieval of a transcatheter pacemaker in sheep after amid-term implantation time", Heart Rhythm Society, Jan. 2016, pp. 43-46, vol. 2-1, Elsevier Inc.
(Continued)

*Primary Examiner* — Jocelin C Tanner
(74) *Attorney, Agent, or Firm* — Seager, Tufte & Wickhem LLP.

(57) ABSTRACT

Extraction devices for extracting chronically implanted devices such as leadless cardiac pacemakers (LCP). In some cases, the extraction devices may be configured to cut or tear through at least some of the tissue ingrowth around and/or over the chronically implanted device such that a retrieval feature on the chronically implanted device may be grasped for removal of the chronically implanted device.

17 Claims, 15 Drawing Sheets

(51) Int. Cl.
  *A61B 17/3205* (2006.01)
  *A61N 1/05* (2006.01)
  *A61B 17/32* (2006.01)
  *A61B 17/3209* (2006.01)
  *A61B 17/34* (2006.01)
  *A61N 1/362* (2006.01)
  *A61B 18/14* (2006.01)
  *A61B 17/00* (2006.01)

(52) U.S. Cl.
  CPC .... *A61B 17/32056* (2013.01); *A61B 17/3468* (2013.01); *A61N 1/056* (2013.01); *A61N 1/362* (2013.01); *A61N 1/372* (2013.01); *A61B 2017/00358* (2013.01); *A61B 2017/320004* (2013.01); *A61B 2017/32006* (2013.01); *A61B 2018/141* (2013.01); *A61N 1/37205* (2013.01); *A61N 2001/0578* (2013.01)

(58) Field of Classification Search
  CPC ......... A61B 2017/320004; A61B 2017/32006; A61B 2018/141; A61N 1/056; A61N 1/362; A61N 1/372; A61N 1/3756; A61N 2001/0578
  See application file for complete search history.

(56) References Cited

U.S. PATENT DOCUMENTS

| | | | |
|---|---|---|---|
| 5,961,526 A * | 10/1999 | Chu | A61B 17/32056 606/113 |
| 6,123,665 A * | 9/2000 | Kawano | A61B 17/3478 600/104 |
| 8,457,742 B2 | 6/2013 | Jacobson | |
| 8,634,919 B1 | 1/2014 | Hou et al. | |
| 8,670,842 B1 | 3/2014 | Bornzin et al. | |
| 8,744,572 B1 | 6/2014 | Greenhut et al. | |
| 8,798,745 B2 | 8/2014 | Jacobson | |
| 8,996,109 B2 | 3/2015 | Karst et al. | |
| 9,020,611 B2 | 4/2015 | Khairkhahan et al. | |
| 9,072,914 B2 | 7/2015 | Greenhut et al. | |
| 9,101,281 B2 | 8/2015 | Reinert et al. | |
| 9,168,372 B2 | 10/2015 | Fain | |
| 9,308,365 B2 | 4/2016 | Nordstrom et al. | |
| 2004/0162554 A1 * | 8/2004 | Lee | A61B 18/14 606/45 |
| 2005/0267555 A1 | 12/2005 | Marnfeldt et al. | |
| 2007/0088394 A1 | 4/2007 | Jacobson | |
| 2007/0250070 A1 * | 10/2007 | Nobis | A61B 17/32056 606/113 |
| 2009/0082828 A1 * | 3/2009 | Ostroff | A61N 1/3756 607/36 |
| 2011/0077680 A1 * | 3/2011 | Heuser | A61B 17/221 606/200 |
| 2011/0112548 A1 * | 5/2011 | Fifer | A61B 17/32001 606/129 |
| 2012/0022558 A1 * | 1/2012 | Friedman et al. | A61B 17/12013 606/139 |
| 2012/0095539 A1 | 4/2012 | Khairkhahan et al. | |
| 2012/0109148 A1 * | 5/2012 | Bonner | A61N 1/372 606/129 |
| 2012/0109149 A1 | 5/2012 | Bonner et al. | |
| 2012/0116489 A1 | 5/2012 | Khairkhahan et al. | |
| 2012/0165827 A1 * | 6/2012 | Khairkhahan | A61B 17/221 606/129 |
| 2012/0226287 A1 * | 9/2012 | Qadeer | A61B 17/00234 606/113 |
| 2013/0079861 A1 | 3/2013 | Reinert et al. | |
| 2013/0116529 A1 | 5/2013 | Min et al. | |
| 2013/0123872 A1 | 5/2013 | Bomzin et al. | |
| 2013/0123875 A1 | 5/2013 | Varady et al. | |
| 2013/0150695 A1 | 6/2013 | Biela et al. | |
| 2013/0211403 A1 | 8/2013 | Suon et al. | |
| 2013/0231710 A1 | 9/2013 | Jacobson | |
| 2013/0303872 A1 | 11/2013 | Taff et al. | |
| 2013/0325081 A1 | 12/2013 | Karst et al. | |
| 2014/0114255 A1 * | 4/2014 | Irwin | A61M 25/0102 604/164.06 |
| 2014/0148675 A1 | 5/2014 | Nordstrom et al. | |
| 2014/0172034 A1 | 6/2014 | Bornzin et al. | |
| 2014/0214104 A1 | 7/2014 | Greenhut et al. | |
| 2014/0257324 A1 | 9/2014 | Fain | |
| 2014/0309706 A1 | 10/2014 | Jacobson | |
| 2015/0051613 A1 | 2/2015 | Schmidt et al. | |
| 2015/0051615 A1 | 2/2015 | Schmidt et al. | |
| 2015/0142069 A1 | 5/2015 | Sambelashvili | |
| 2015/0142070 A1 | 5/2015 | Sambelashvili | |
| 2015/0165199 A1 | 6/2015 | Karst et al. | |
| 2015/0297905 A1 | 10/2015 | Greenhut et al. | |
| 2015/0305768 A1 | 10/2015 | Harrah et al. | |
| 2015/0306381 A1 | 10/2015 | Schmidt et al. | |
| 2015/0335884 A1 | 11/2015 | Khairkhahan et al. | |
| 2016/0242804 A1 * | 8/2016 | Fleury | A61B 17/32056 |
| 2017/0281261 A1 | 10/2017 | Shuros et al. | |

FOREIGN PATENT DOCUMENTS

| | | |
|---|---|---|
| WO | 2010141189 A1 | 12/2010 |
| WO | 2015168155 A1 | 11/2015 |

OTHER PUBLICATIONS

Sperzel et al., "State of the art of leadless pacing", European Society of Cardiology, 2015, pp. 1508-1513, vol. 15, Oxford University Press.

Invitation to Pay Additional Fees dated Jun. 13, 2017 for International Application No. PCT/US2017/025180.

* cited by examiner

EXTRACTION DEVICES CONFIGUED TO EXTRACT CHRONICALLY IMPLANTED MEDICAL DEVICES

CROSS REFERENCE TO RELATED APPLICATIONS

This application claims the benefit of U.S. Provisional Patent Application Ser. No. 62/316,074 filed on Mar. 31, 2016, the disclosure of which is incorporated herein by reference.

TECHNICAL FIELD

The disclosure relates generally to extraction devices, and more particularly to extraction devices for extracting chronically implanted medical devices.

BACKGROUND

Cardiac pacemakers such as leadless cardiac pacemakers are used to sense and pace hearts that are susceptible to a variety of incorrect heart rhythms, including but not limited to bradycardia, which is a slow heart rate, and tachycardia, which is a high heart rate. In some cases, there may be a desire to remove a previously implanted leadless cardiac pacemaker. Since these devices are designed for long life, in many cases substantial tissue growth (e.g. endothelialization) around and even over the leadless cardiac pacemaker may occur, particularly with chronically (long-term) implanted devices. Tissue growth can complicate removal of the implanted device. Accordingly, there is a desire to provide extraction devices that are directed at extracting chronically implanted devices such as but not limited to leadless cardiac pacemakers.

SUMMARY

The disclosure is directed to extraction devices that are configured to extract chronically implanted devices such as but not limited to leadless cardiac pacemakers (LCP). In some cases, these devices may be configured to cut or tear through at least some of the tissue ingrowth around and/or over the chronically implanted device such that a retrieval feature on the chronically implanted device may be grasped for removal of the chronically implanted device.

In an example of the disclosure, an extraction device may be used for removing a previously implanted LCP that includes a retrieval feature disposed at a proximal end of the LCP. The extraction device includes a retrieval cavity at a distal region of the extraction device that is sized to accommodate at least part of the LCP therein once the LCP is extracted. A retrieval loop may be extendable beyond the retrieval cavity and manipulatable from the proximal region of the extraction device by an operator (e.g. physician). An inside surface of the retrieval loop may be configured to cut through ingrowth tissue that extends over the LCP in order to expose the retrieval feature of the LCP. The retrieval loop may also be configured to grasp the exposed retrieval feature and pull the LCP into the retrieval cavity of the extraction device.

Alternatively or additionally to any of the embodiments above, the retrieval loop may form at least part of a loop with a first surface on an inner side of the loop and a second surface on an outer side of the loop, wherein the first surface is configured to cut tissue better than the second surface.

Alternatively or additionally to any of the embodiments above, the first surface may include an abrasive material and the second surface may not include the abrasive material.

Alternatively or additionally to any of the embodiments above, the first surface may include a cutting edge and the second surface may be smooth.

Alternatively or additionally to any of the embodiments above, the cutting edge may include a plurality of teeth.

Alternatively or additionally to any of the embodiments above, at least a portion of the inside surface of the retrieval loop may be electrically exposed to conduct RF energy to cut through the ingrowth tissue.

Alternatively or additionally to any of the embodiments above, the extraction device may include a funnel that is configured to be extended relative to the retrieval cavity.

Alternatively or additionally to any of the embodiments above, the funnel may be configured to be rotatable and may include a cutting surface on an interior of the funnel in order to cut through and/or tear away ingrowth tissue covering the retrieval feature of the implanted leadless cardiac pacemaker.

In another example of the disclosure, an extraction device may be used for removing a previously implanted LCP that includes a retrieval feature disposed at a proximal end of the LCP. The extraction device may include a retrieval cavity at a distal region of the extraction device that is sized to accommodate at least part of the LCP therein once the leadless cardiac pacemaker is extracted. An extractor member may be extendable beyond the retrieval cavity and may be configured to cut through ingrowth tissue that extends over the LCP in order to expose the retrieval feature of the LCP.

Alternatively or additionally to any of the embodiments above, the extractor member may include a hollow needle that is fluidly coupled with a fluid source in order to inject a fluid in a space between the implanted leadless cardiac pacemaker and the ingrowth tissue.

Alternatively or additionally to any of the embodiments above, the extraction device may include a preshaped cutting stylet that is extendable through the hollow needle and under the ingrown tissue in order to cut through the ingrowth tissue.

Alternatively or additionally to any of the embodiments above, the extractor member may include a deflectable probe that is configured to pierce and cut through the ingrowth tissue.

Alternatively or additionally to any of the embodiments above, the extractor member may include a grasping forceps configured to grasp and tear at the ingrowth tissue.

Alternatively or additionally to any of the embodiments above, the grasping forceps may be electrically active and can transmit RF energy in order to cut the ingrowth tissue.

Alternatively or additionally to any of the embodiments above, the extraction device may further include a retrieval loop that is extendable beyond the retrieval cavity and manipulatable from the proximal region of the extraction device by an operator, wherein the retrieval loop is manipulatable to grasp the retrieval feature of the implanted LCP and pull the implanted LCP into the retrieval cavity.

As noted above, a retrieval loop may be used for removing a previously implanted LCP. In some instances, the retrieval loop may include a first surface and an opposing second surface, wherein the first surface is configured to cut tissue better than the opposing second surface.

Alternatively or additionally to any of the embodiments above, the retrieval loop may form at least part of a loop with the first surface on an inner side of the loop and the second surface on an outer side of the loop, wherein the first surface includes one or more cutting features and the second surface is free from cutting features.

Alternatively or additionally to any of the embodiments above, the first surface may include abrasive material and the second surface may not include the abrasive material.

Alternatively or additionally to any of the embodiments above, the first surface may include a cutting edge and the second surface may be free from a cutting edge.

Alternatively or additionally to any of the embodiments above, at least a portion of the first surface may be electrically exposed to conduct applied RF energy to the ingrowth tissue to cut through the ingrowth tissue, and the second surface may not be electrical exposed so as to substantially insulate the adjacent tissue from the applied RF energy.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE FIGURES

The disclosure may be more completely understood in consideration of the following detailed description in connection with the accompanying drawings, in which.

Figure 1:
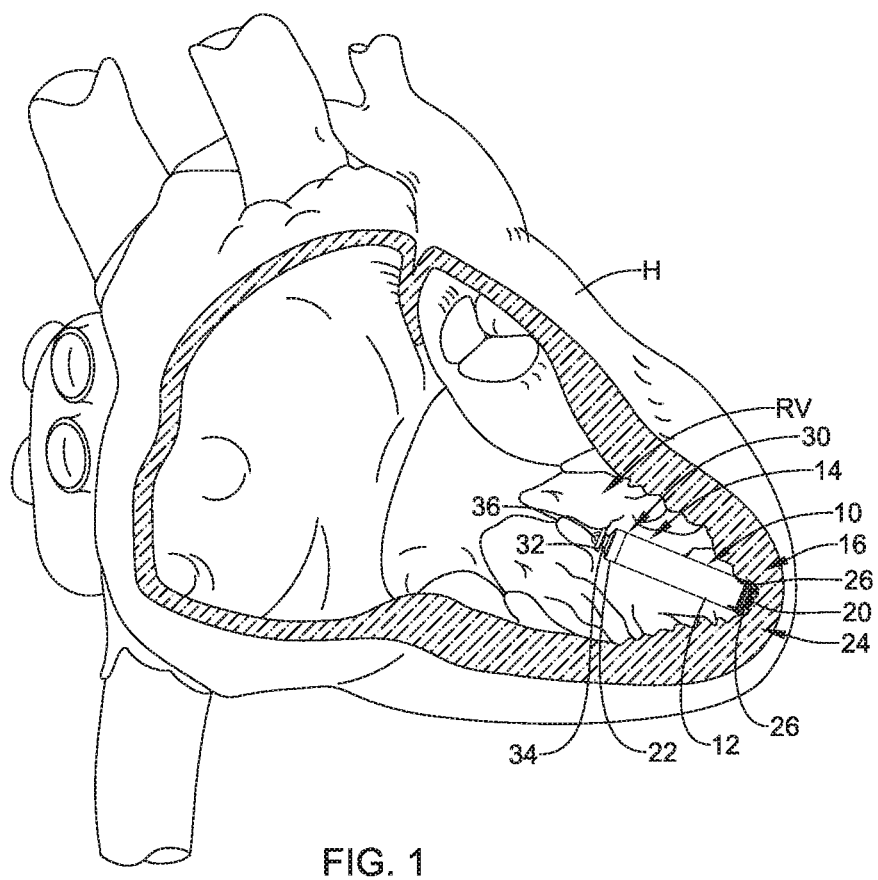
FIG. 1 is a partial cut away plan view of an example leadless pacing device implanted within a heart.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers may include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules that may, for example, be fixed to an intracardiac implant site in a cardiac chamber. In some cases, the small capsule may include bipolar pacing/sensing electrodes, a power source (e.g. a battery), and associated electrical circuitry for controlling the pacing/sensing electrodes, and thus may provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle.

While a leadless cardiac pacemaker is used as an example implantable medical device, the disclosure may be applied to any suitable implantable medical device including, for example, neuro-stimulators, diagnostic devices including those that do not deliver therapy, and/or any other suitable implantable medical device as desired.

Figure 2:
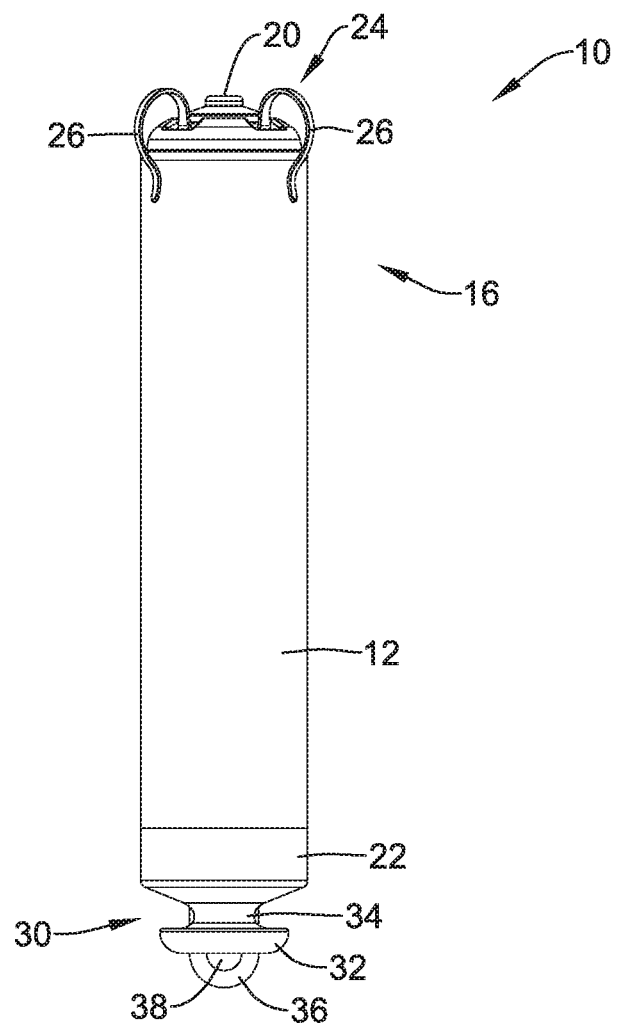
FIG. 2 is a side elevation view of an example implantable LCP device.

FIG. 1 illustrates an example implantable leadless cardiac pacing device 10 (e.g., a leadless pacemaker) implanted in a chamber of a heart H, such as the right ventricle RV. A side elevation view of the illustrative implantable medical device (IMD) 10 is shown in FIG. 2. The implantable device 10 may include a shell or housing 12 having a proximal end 14 and a distal end 16. In some instances, the IMD 10 may include a first electrode 20 positioned adjacent to the distal end 16 of the housing 12, and a second electrode 22 positioned adjacent to the proximal end 14 of the housing 12. In some cases, the housing 12 may include a conductive material and may be insulated at least a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be configured to be positioned against the cardiac tissue of the heart H or may otherwise contact the cardiac tissue of the heart H while the second electrode 22 may be spaced away from the first electrode 20, and thus spaced away from the cardiac tissue.

The illustrative IMD 10 may include a pulse generator (e.g., electrical circuitry) and a power source (e.g., a battery) within the housing 12 to provide electrical signals to the electrodes 20, 22 and thus control the pacing/sensing electrodes 20, 22. In some cases, electrical communication between the pulse generator and the electrodes 20, 22 may provide electrical stimulation to heart tissue and/or sense a physiological condition.

The IMD 10 may include a fixation mechanism 24 proximate the distal end 16 of the housing 12 configured to attach the IMD 10 to a tissue wall of the heart H, or otherwise anchor the IMD 10 to the anatomy of the patient. As shown in FIG. 1, in some instances, the fixation mechanism 24 may include one or more, or a plurality of hooks or tines 26 anchored into the cardiac tissue of the heart H to attach the IMD 10 to a tissue wall. In other cases, the fixation mechanism 24 may include one or more, or a plurality of passive tines, configured to entangle with trabeculae within the chamber of the heart H and/or a helical fixation anchor configured to be screwed into a tissue wall to anchor the IMD 10 to the heart H. These are just some examples.

The IMD 10 may include a docking member 30 proximate the proximal end 14 of the housing 12 configured to facilitate delivery and/or retrieval of the IMD 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the IMD 10 which is greater than a radial dimension of the neck portion 34 from the longitudinal axis of the IMD 10. In some cases, the docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g. looped) through the opening 38. The docking member 30 may be configured to facilitate delivery of the IMD 10 to the intracardiac site and/or retrieval of the IMD 10 from the intracardiac site. FIG. 2 shows one example docking member configuration. However, it is contemplated that any suitable docking member configuration may be used, as desired.

In some cases, the docking member 30, or at least a portion thereof, may be considered as providing a retrieval feature generally shown at 40 that may subsequently be grasped in order to retrieve the IMD 10 subsequent to implantation. The retrieval feature 40 may be grasped, for example, by a variety of different devices, such as but not limited to a retrieval loop, forceps and the like. In some cases, retrieval of a chronically implanted IMD 10, meaning that the IMD 10 has been in place within the anatomy for a period of time ranging from several months to multiple years, may be complicated by tissue ingrowth around part or even all of the IMD 10, including the retrieval feature 40. In some cases, it may be useful to cut through or otherwise remove at least some of the tissue ingrowth prior to actually retrieving the IMD 10.

Figure 3:
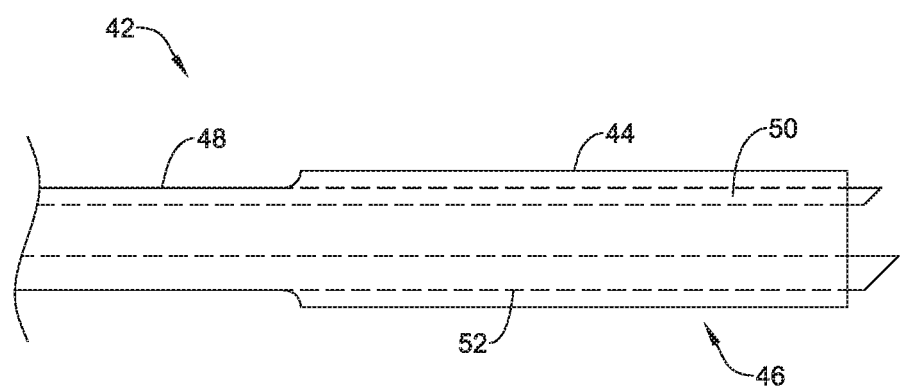
FIG. 3 is a schematic view of an illustrative extraction device according to an example of the disclosure.

FIG. 3 provides a highly schematic view of a distal portion of an illustrative extraction device 42. The illustrative extraction device 42 includes a retrieval cavity 44 disposed at a distal region 46 of the extraction device 42. The more proximal portions of the extraction device 42 are not shown, including a proximal portion that may be manipulated by an operator of the extraction device. In some cases, the retrieval cavity 44 is sized and otherwise configured to accommodate at least part of the IMD 10 therein once the IMD 10 has been extracted from the heart tissue and has been withdrawn into the retrieval cavity 44. In some cases, the retrieval cavity 44 has a length sufficient to accommodate the entire IMD 10, and the retrieval cavity 44 has an inner diameter that is sufficient to accommodate the IMD 10. In some cases, the retrieval cavity 44 has an inner diameter that is sufficient to simultaneously accommodate the IMD 10 as well as one or more additional tools or other devices extending through the extraction device 42 and into the retrieval cavity 44. In some cases, the retrieval cavity 44 extends distally from an extraction device shaft 48.

In some cases, as noted, other tools and other devices may be used in combination with the extraction device 42, and/or may be included as part of the extraction device 42. As seen in FIG. 3, a relatively smaller diameter tool 50 and a relatively larger diameter tool 52, seen in phantom, may be disposed within and extend distally from the retrieval cavity 44. In some cases, the relatively smaller diameter tool 50 may represent a retrieval loop, or a needle, or perhaps a wire that can be bent into a shape to cut into ingrowth tissue. In some cases, the relatively larger diameter tool 52 may represent a pair of grasping forceps, or perhaps a funnel that can be extended to help cut through ingrowth tissue. Illustrative but non-limiting examples of these tools 50, 52 will be discussed with respect to subsequent Figures. In each of the subsequent Figures, the IMD 10 is shown as being an LCP 54 including a retrieval feature 56, and is covered or at least substantially covered by ingrowth tissue 58.

Figure 4:
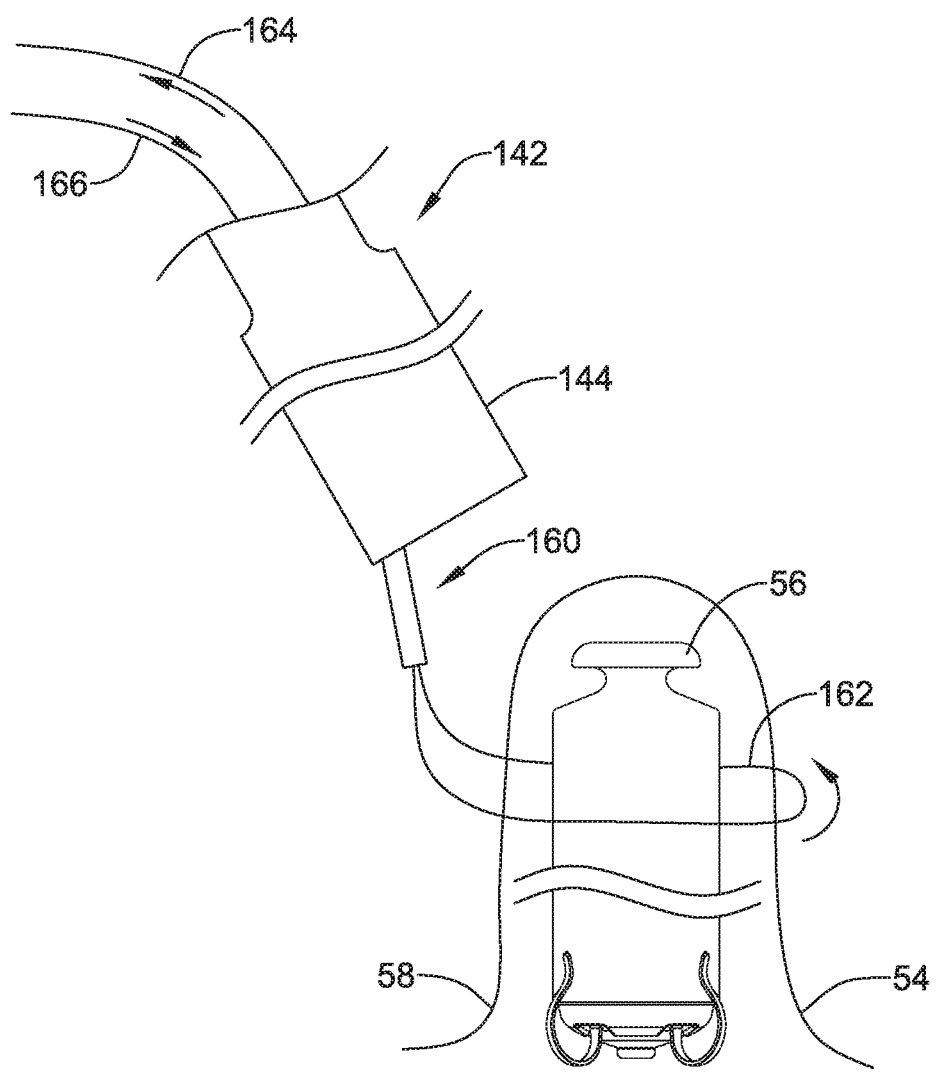
FIG. 4 is a schematic view of an illustrative extraction device extracting a chronically implanted LCP according to an example of the disclosure.

FIG. 4 is a schematic diagram of an illustrative extraction device 142, which may be considered as being an example of the extraction device 42 (FIG. 3). A distal portion of the illustrative extraction device 142 includes a retrieval cavity 144. The more proximal portions of the extraction device 142 are not shown, including a proximal portion that may be manipulated by an operator of the extraction device. The retrieval loop 160 may include a loop 162 and first and second control wires 164, 166. The loop 162 may extend distally from the retrieval cavity 144. In some cases, the retrieval loop 160 may be considered as being an example of the relatively smaller diameter tool 50 (FIG. 3), but this is not required. In some cases, the first and second control wires 164, 166 may be electrically active, and a portion of the loop 162 may be electrically exposed in order to conduct RF energy for the purposes of cutting through at least some of the ingrowth tissue 58. In some cases, a cutaneous patch (not shown) may be used as a return electrode.

It will be appreciated that by moving the first and second control wires 164, 166 together, the loop 162 may be advanced distally from the retrieval cavity 144 or withdrawn proximally towards and into the retrieval cavity 144. Appropriate manipulation of the first and second control wires 164, 166 may also be used to make the loop 162 smaller or larger, as desired. Manipulation of the first and second control wires 164, 166 in opposite directions may be used to slide a portion of the loop 162 back and forth relative to the ingrowth tissue 58 in a cutting motion. After cutting away sufficient ingrowth tissue 58 using the retrieval loop 160 to expose and then grasp the retrieval feature 40, the retrieval loop 160 may be withdrawn proximally to pull the LCP 54 into the receiving cavity 144.

Figure 5:
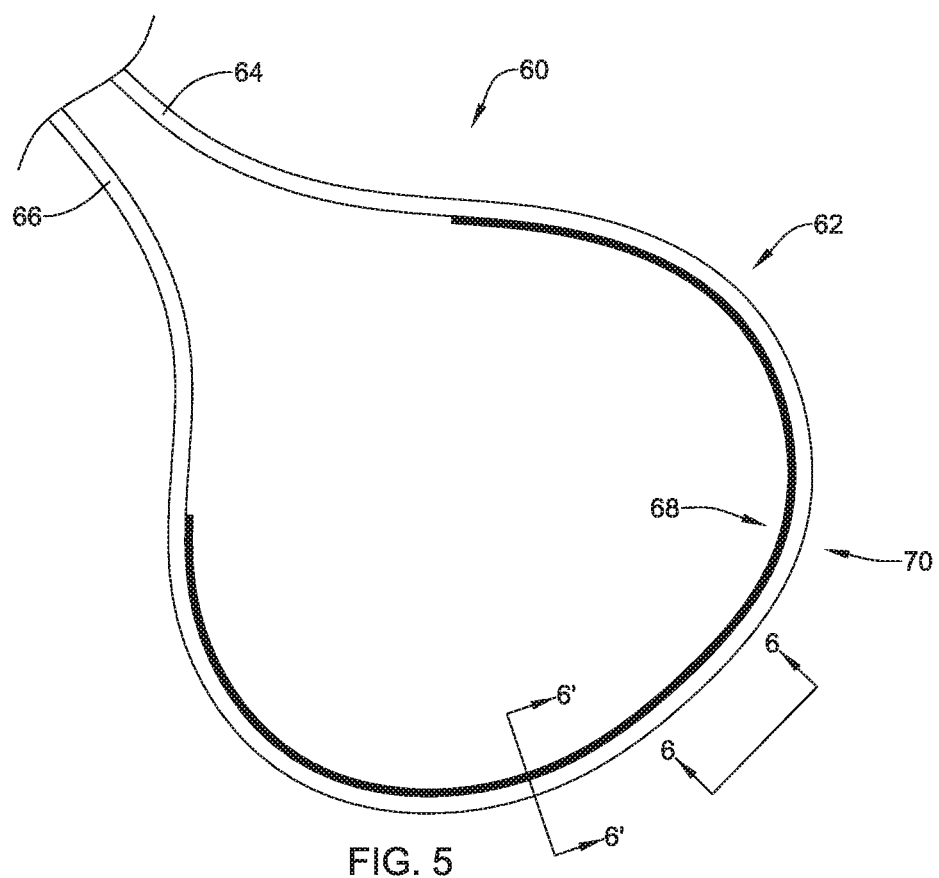
FIG. 5 is an enlarged view of an illustrative retrieval loop forming part of the extraction device of FIG. 4.

In some cases, the loop 162 may be configured to cut or tear through the ingrowth tissue 58 as the loop 162 moves relative to the ingrowth tissue 58. FIG. 5 is an enlarged view of an illustrative retrieval loop 160. As can be seen in FIG. 5, in some cases the retrieval loop forms a loop 162 that has an inside surface 168 and an outer surface 170. In some cases, the inside surface 168, or a first surface, may be configured to cut, abrade or otherwise disrupt the ingrowth tissue 58. In some cases, the outer surface 170, or a second surface, may not be configured to cut, abrade or otherwise disrupt the ingrowth tissue 58. In some cases, the outside surface may be smooth. As a result, the inside surface 168 may be used to cut through the ingrowth tissue 58 while the outer surface 170 may be configured to not damage other nearby tissue (e.g. the heart wall). In some cases, the loop 162 may be used to cut around the LCP 54, exposing the retrieval feature 40. With reference to FIG. 4, once the retrieval feature 40 is exposed, the loop 162 may be tightened around the retrieval feature 40 of the LCP 54, and then may be used to pull the LCP 54 into the retrieval cavity 144. Once the LCP is in the retrieval cavity 144, the extraction device and the LCP 54 may be removed from the body.

Figure 6A:
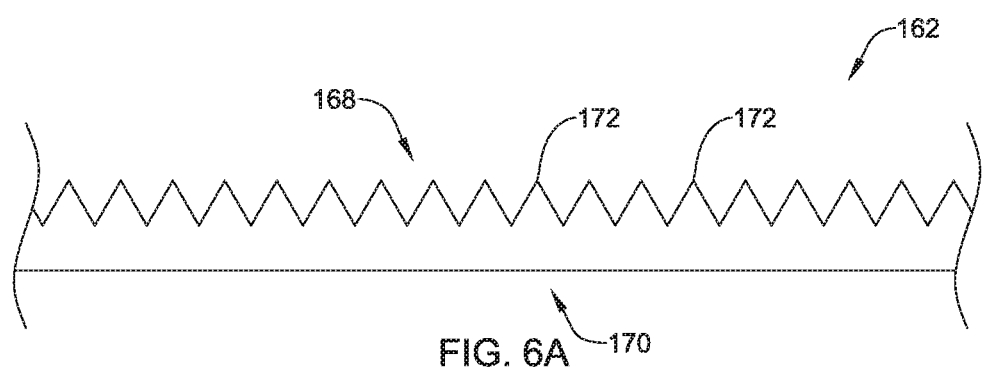
FIGS. 6A and 6B are enlarged schematic views of two example cutting surfaces of the illustrative retrieval loop of FIG. 5, taken along line 6-6 of FIG. 5.
Figure 6B:
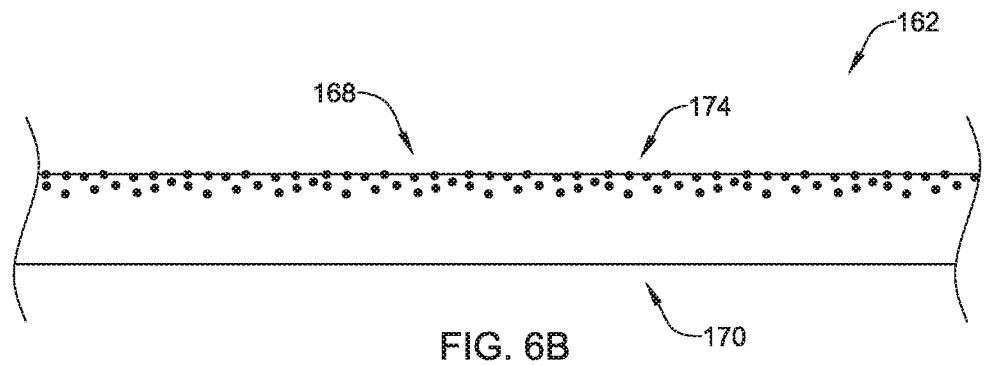
Figure 6C:
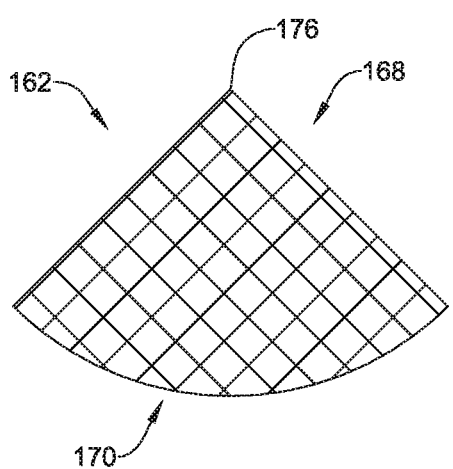
FIG. 6C is a schematic cross-sectional view showing an illustrative cutting surface of the illustrative retrieval loop of FIG. 5, taken along line 6'-6' of FIG. 5.

FIGS. 6A and 6B are enlarged schematic views of two example cutting surfaces of the illustrative retrieval loop of FIG. 5, taken along line 6-6 of FIG. 5. In both FIG. 6A and FIG. 6B, the loop 162 includes an inside surface 168 and an outer surface 170. In FIG. 6A, the inside surface 168 includes a plurality of teeth 172. It will be appreciated that as the loop 162 is slide back and forth relative to the ingrowth tissue 58, the teeth 172 will cut through the ingrowth tissue 58. In this example, the outer surface 170 is relatively smooth. In FIG. 6B, the inside surface 168 includes an abrasive surface 174. In some cases, the abrasive surface 174 may include an abrasive material that is deposited onto the inside surface 168. In some cases, the abrasive surface 174 may instead be the result of etching the inside surface 168 to form a roughened and abrasive surface. In the example shown, the outer surface 170 does not include the abrasive surface 174, and instead is relatively smooth to limit peripheral tissue damage during use of the retrieval loop 162. FIG. 6C is a cross-sectional view through the loop 162, and shows another example in which the inside surface 68 has a blade-like cutting surface 176 which may, for example, may cut more smoothly through the ingrowth tissue 58, and in some cases may tear less.

Figure 7:
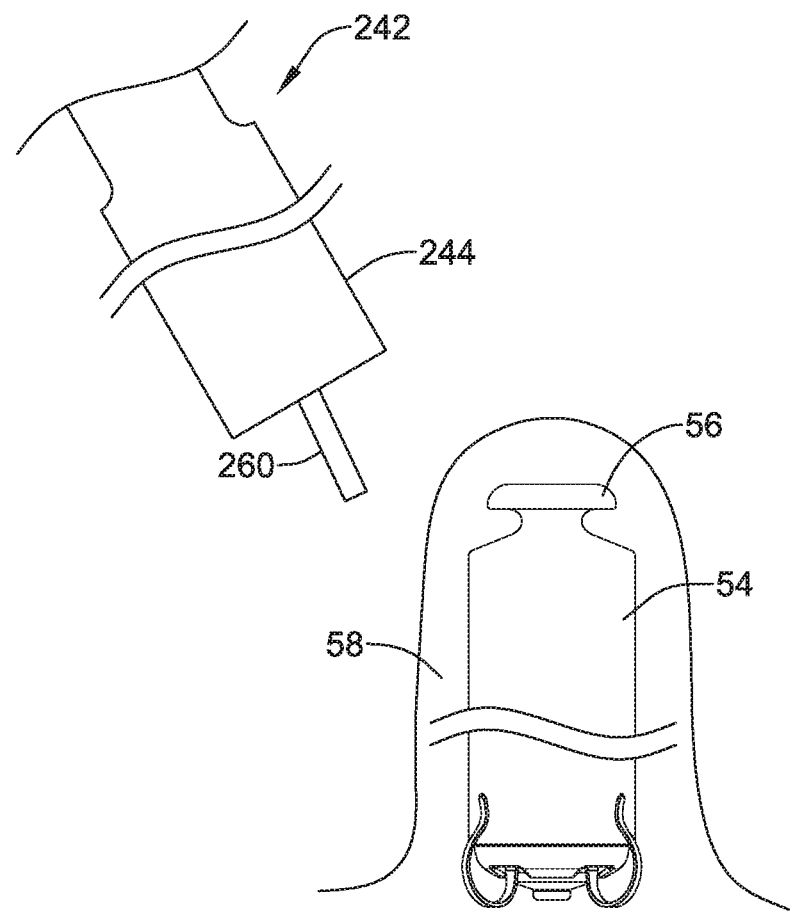
FIG. 7 is a schematic view of an illustrative extraction device extracting a chronically implanted LCP according to an example of the disclosure.

FIG. 7 is a schematic illustration of another illustrative extraction device 242, which may be considered as being an example of the extraction device 42 (FIG. 3). A distal portion of the illustrative extraction device 242 includes a retrieval cavity 244. The more proximal portions of the extraction device 242 are not shown, including a proximal portion that may be manipulated by an operator of the extraction device. In this example, a hollow needle 260 may be extended from the retrieval cavity 244 and may for example be considered as an example of the relatively larger tool 52 (FIG. 3). In some cases, the hollow needle 260 may be in fluid communication with a source (not shown) of saline, or perhaps contrast solution such that the hollow needle 260 may be able to penetrate through the ingrowth tissue 58 and reach a location proximate the LCP 54. Injecting fluid through the hollow needle 260 may, for example, help to loosen some of the ingrowth tissue 58 away from the outer surface of the LCP 54. Penetrating the ingrowth tissue 58 may also help reduce a vacuum that might otherwise develop when attempting to withdraw the LCP 54 from the ingrowth tissue 58.

Figure 8:
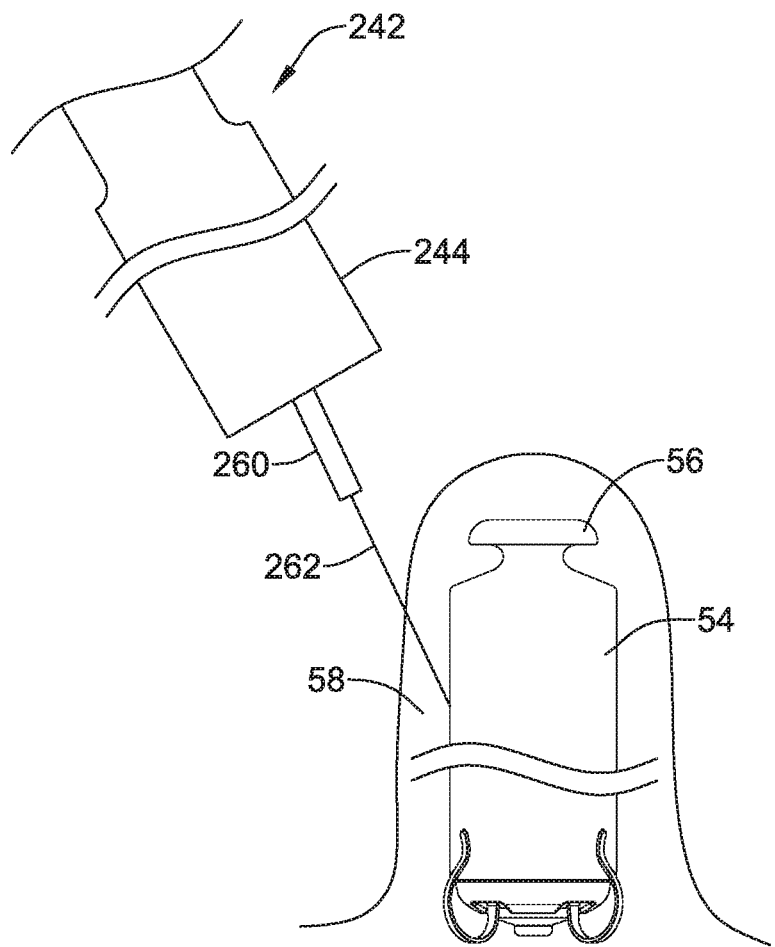
FIG. 8 is a schematic view of an illustrative extraction device extracting a chronically implanted LCP according to an example of the disclosure.

In some cases, as shown in FIG. 8, an elongated probe 262 may be advanced through the hollow needle 260 (or advanced adjacent the hollow needle 260) and may be moved about the LCP 54 in a radial direction indicated by an arrow 264 to score and break away some of the ingrowth tissue 58. The elongated probe 262 may have a pre-bent shape that it assumes once advanced out of the hollow needle 260 and may have a cutting edge. The pre-bent shape may be configured to bend around and track the outer surface of the housing of the LCP 54, as shown. In some cases, the elongated probe 262 may be considered a pre-shaped cutting stylet.

The elongated probe 262 may be moved longitudinally along the length of the housing of the LCP to separate the ingrowth tissue 58 from the housing of the LCP 54, and to cut the ingrowth tissue to expose the retrieval feature 56 of the LCP 54. In some cases, the hollow needle 260 (and elongated probe 262) may then be withdrawn and a retrieval loop such as the retrieval loop 60 (FIG. 4) may be advanced to engage the retrieval feature 56 and withdraw the LCP 54 into the retrieval cavity 244.

Figure 9:
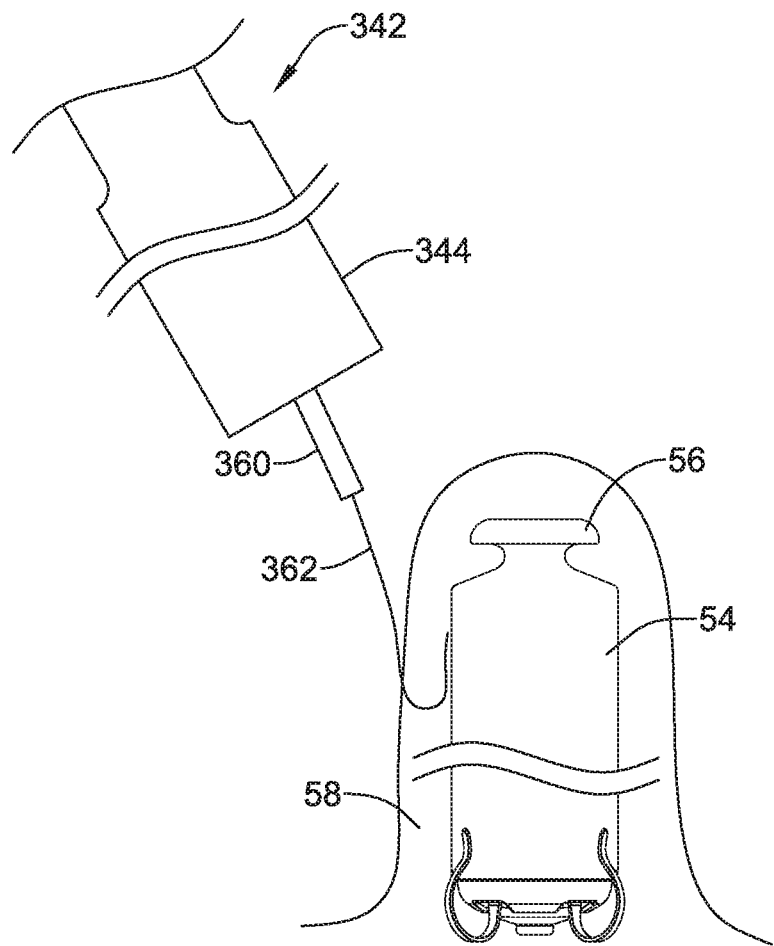
FIG. 9 is a schematic view of an illustrative extraction device extracting a chronically implanted LCP according to an example of the disclosure.

FIG. 9 is a schematic illustration of another illustrative extraction device 342, which may be considered as being an example of the extraction device 42 (FIG. 3). A distal portion of the illustrative extraction device 342 includes a retrieval cavity 344. The more proximal portions of the extraction device 342 are not shown, including a proximal portion that may be manipulated by an operator of the extraction device. In the example shown, a deflectable probe 360 may be advanced distally from the retrieval cavity 344 and may be used to penetrate into the ingrowth tissue 58. In some cases, the deflectable probe 360 may be considered as extending from an elongate tube 362, which in some cases may be considered as being an example of the relatively larger diameter tool 52 (FIG. 3). Penetrating the ingrowth tissue 58 may also help reduce a vacuum that might otherwise develop when attempting to withdraw the LCP 54 from the ingrowth tissue 58. The deflectable probe 360 may, in some cases, be deflected into a hook-shape once advanced out of the elongated tube 362. The hook can be withdrawn proximally to tear or otherwise remove some of the ingrowth tissue 58 to expose the retrieval feature 56 of the LCP 54. In some cases, the deflectable probe 360 may then be withdrawn and a retrieval loop such as the retrieval loop 60 (FIG. 4) may be advanced to engage the retrieval feature 56 and withdraw the LCP 54 into the retrieval cavity 344.

Figure 10:
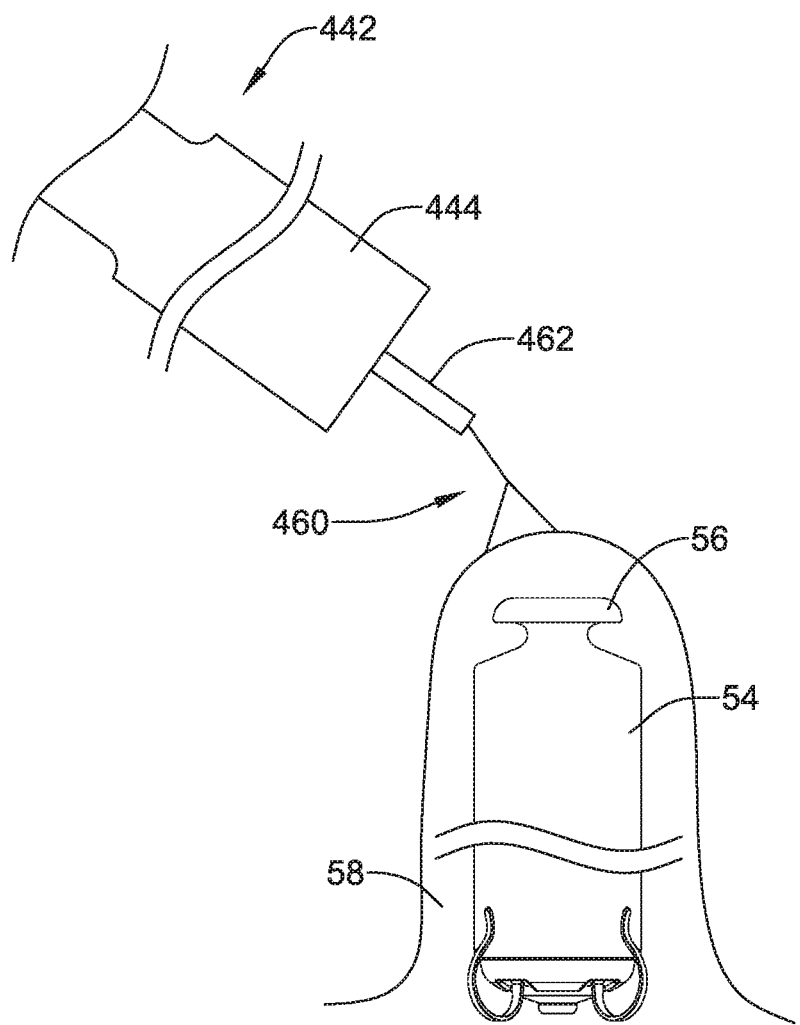
FIG. 10 is a schematic view of an illustrative extraction device extracting a chronically implanted LCP according to an example of the disclosure.

FIG. 10 is a schematic diagram of another illustrative extraction device 442, which may be considered as being an example of the extraction device 42 (FIG. 3). A distal portion of the illustrative extraction device 442 includes a retrieval cavity 444. The more proximal portions of the extraction device 442 are not shown, including a proximal portion that may be manipulated by an operator of the extraction device. In some cases, a grasping forceps 460 may be distally extendable from an elongate tube 462 that may, for example, be considered as being an example of the relatively larger diameter tool 52 (FIG. 3). The grasping forceps 460 may be used to grasp and tear away at the ingrowth tissue 58. In some cases, the grasping forceps 460 may be electrically active and may be used to transmit RF energy to cut the ingrowth tissue. Once the retrieval feature 56 is exposed, the grasping forceps 460 may be used to engage the retrieval feature 56 and withdraw the LCP 54 into the retrieval cavity 444. In other cases, the grasping forceps 460 may be withdrawn, and a retrieval loop such as the retrieval loop 60 (FIG. 4) may be advanced to engage the retrieval feature 56 and withdraw the LCP 54 into the retrieval cavity 444.

Figure 11:
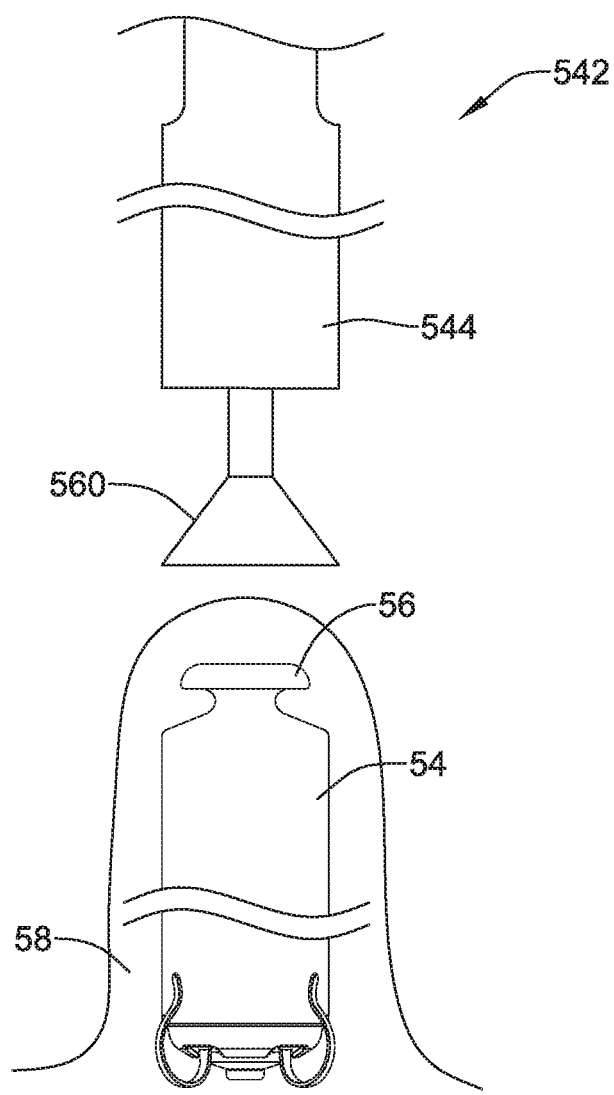
FIG. 11 is a schematic view of an illustrative extraction device extracting a chronically implanted LCP according to an example of the disclosure.
Figure 12:
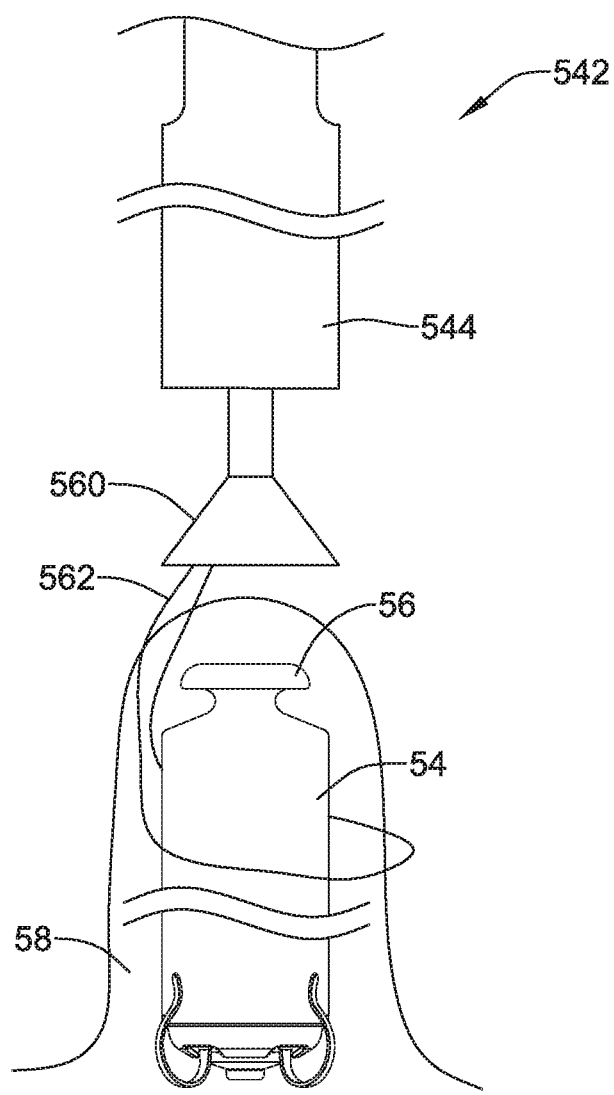
FIG. 12 is a schematic view of an illustrative extraction device extracting a chronically implanted LCP according to an example of the disclosure.
Figure 14:
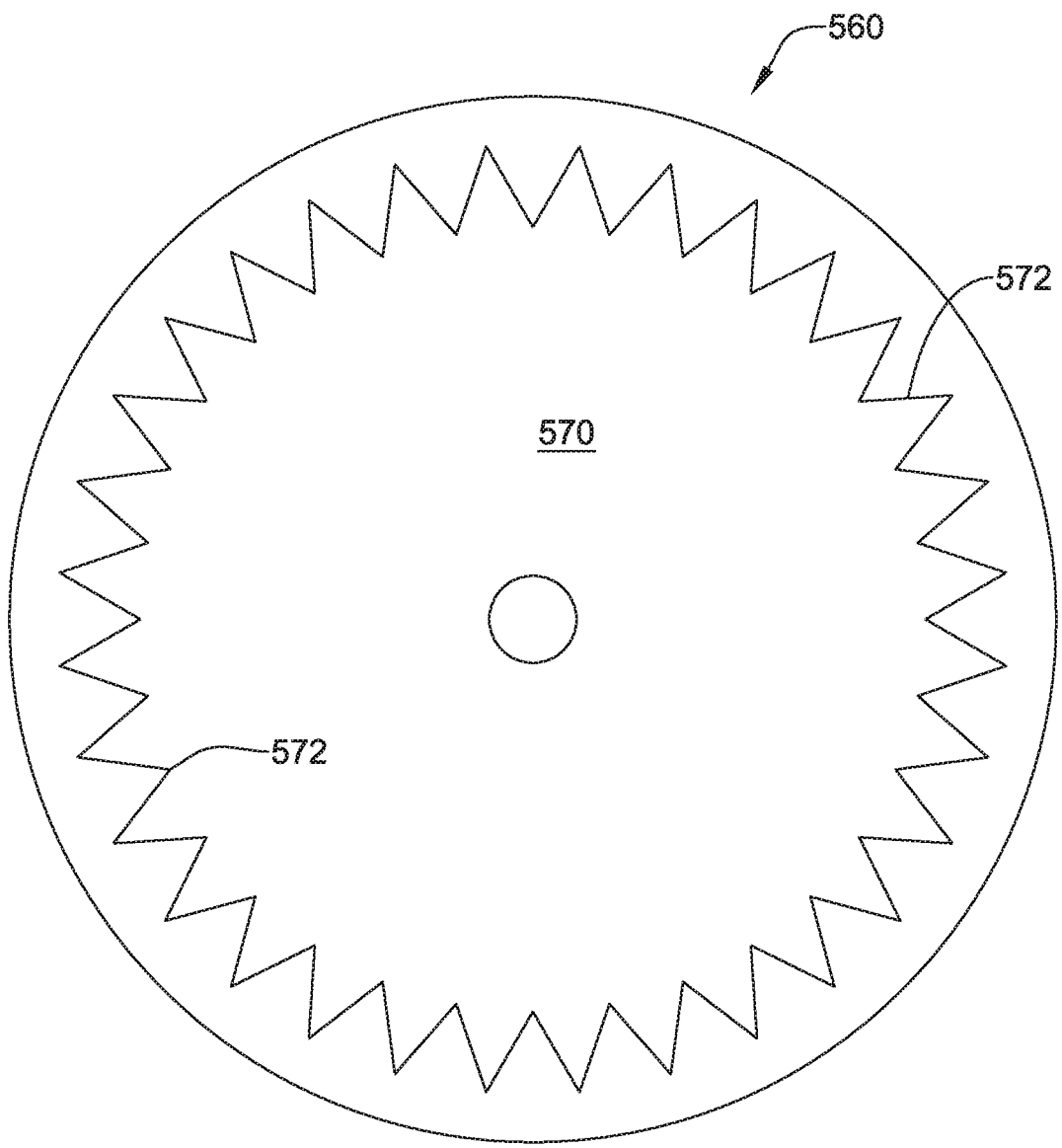
FIG. 14 is an enlarged view of a mouth of the funnel used in the extraction devices shown in FIGS. 11 through 13.

FIG. 11 is a schematic diagram of an illustrative extraction device 542, which may be considered as being an example of the extraction device 42 (FIG. 3). A distal portion of the illustrative extraction device 542 includes a retrieval cavity 544. The more proximal portions of the extraction device 242 are not shown, including a proximal portion that may be manipulated by an operator of the extraction device. In this example, an extendable funnel 560 is extendable from the retrieval cavity 544. In some cases, as shown for example in FIG. 14, the extendable funnel 560 may include a plurality of teeth 572 disposed on an inner surface 570 of the extendable funnel 560. As a result, and returning to FIG. 11, the extendable funnel 560 may be advanced into contact with the ingrowth tissue 58 and then rotated to cut through the ingrowth tissue 58. In some cases, the extendable funnel 560 may be considered as being an example of the relatively larger diameter tool 52 (FIG. 3). Once the retrieval feature 56 is exposed, and as shown in FIG. 12, a retrieval loop 562 (much like the retrieval loop 60 of FIG. 4) may be advanced, sometimes through the extendable funnel 560 or adjacent the extendable funnel 560, to engage the retrieval feature 56 and withdraw the LCP 54 into the retrieval cavity 344.

Figure 13:
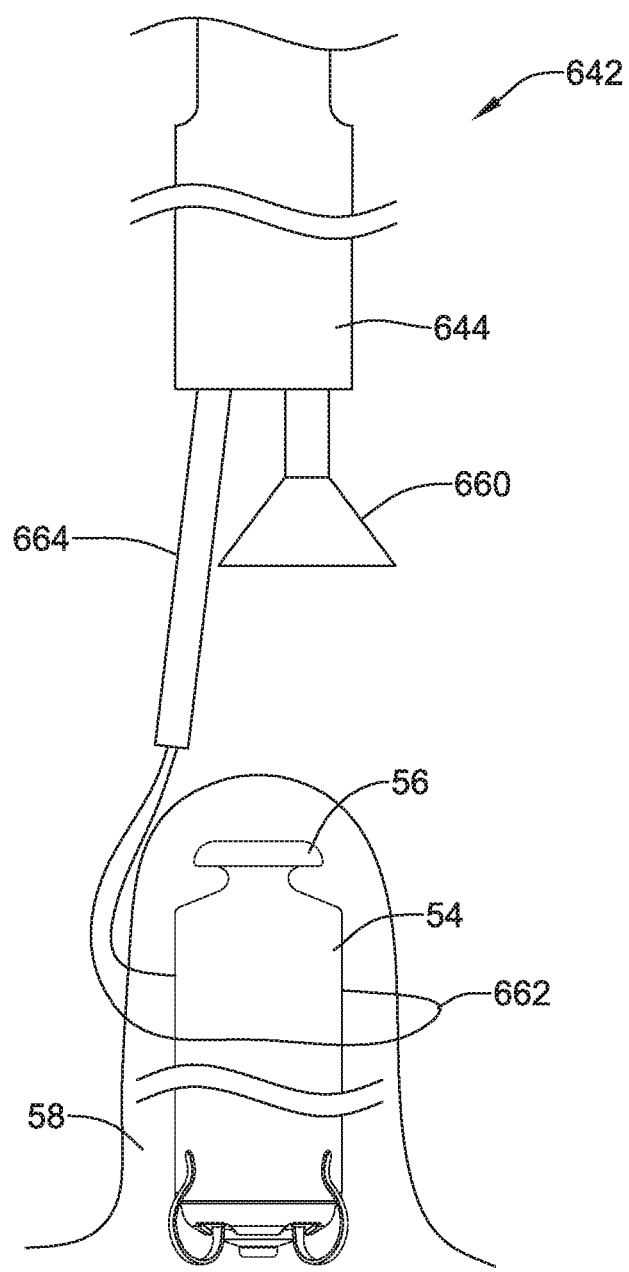
FIG. 13 is a schematic view of an illustrative extraction device extracting a chronically implanted LCP according to an example of the disclosure.

FIG. 13 is a schematic diagram of an illustrative extraction device 642, which may be considered as being an example of the extraction device 42 (FIG. 3). A distal portion of the illustrative extraction device 642 includes a retrieval cavity 644. The more proximal portions of the extraction device 642 are not shown, including a proximal portion that may be manipulated by an operator of the extraction device. The extraction device 642 is similar to the extraction device 542, including an extendable funnel 660, and a retrieval loop 662, but also includes a retrieval loop sheath 664. In some cases, the retrieval loop sheath 664 may be located off-center within the retrieval cavity 644. In some cases, this permits other tools to be inserted distally through the retrieval cavity 644 in a more centered orientation. In some cases, the extendable funnel 660 includes internally located teeth, much like the teeth 572 shown in FIG. 14.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. An extraction system for removing a chronically implanted Leadless Cardiac Pacemaker (LCP), the system comprising:
    a chronically implanted Leadless Cardiac Pacemaker (LCP), the LCP including a retrieval feature disposed on a proximal region of the LCP; and
    an extraction device having a proximal region and a distal region, the extraction device comprising:
        a retrieval cavity at the distal region of the extraction device that is configured to be sized to accommodate at least part of the LCP therein once the LCP is extracted;
        a retrieval loop including first and second control wires, the retrieval loop is configured to be extendable beyond the retrieval cavity by moving the first and/or second control wires and around the LCP and any ingrowth tissue that extends over the LCP as a result of the LCP having been chronically implanted, the first and second control wires of the retrieval loop configured to be manipulatable from the proximal region by an operator of the extraction device;
        with the retrieval loop configured to be manipulated around the LCP and any ingrowth tissue that extends over the LCP as a result of the LCP having been chronically implanted, the retrieval loop is configured along an inside surface of the retrieval loop to cut through any ingrowth tissue that extends over the LCP as a result of the LCP having been chronically implanted by moving the first and/or second control wires to thereby expose the retrieval feature of the LCP; and
        the retrieval loop is further configured to then grasp the exposed retrieval feature and pull the LCP into the retrieval cavity of the extraction device by moving the first and/or second control wires.

2. The extraction system of claim 1, wherein the retrieval loop forms at least part of a loop with a first surface on an inner side of the loop and a second surface on an outer side of the loop, wherein the first surface is configured to cut tissue better than the second surface.

3. The extraction system of claim 2, wherein the first surface comprises an abrasive material and the second surface does not include the abrasive material.

4. The extraction system of claim 2, wherein the first surface comprises a cutting edge and the second surface is smooth.

5. The extraction system of claim 4, wherein the cutting edge includes a plurality of teeth.

6. The extraction system of claim 1, wherein at least a portion of the inside surface of the retrieval loop is electrically exposed to conduct RF energy to cut through any ingrowth tissue.

7. The extraction system of claim 1, further comprising an extendable funnel that is configured to be extended relative to the retrieval cavity.

8. The extraction system of claim 7, wherein the extendable funnel is configured to be rotatable and includes a cutting surface on an interior of the extendable funnel in order to cut through ingrowth tissue covering the retrieval feature of the implanted LCP.

9. An extraction system for removing a chronically implanted Leadless Cardiac Pacemaker (LCP), the system comprising:
- a chronically implanted Leadless Cardiac Pacemaker (LCP), the LCP including a retrieval feature disposed on a proximal region of the LCP, wherein as a result of the LCP having been chronically implanted, there is ingrowth tissue extending over at least part of the retrieval feature; and
- an extraction device having a proximal region and a distal region, the extraction device comprising:
  - a retrieval cavity at the distal region of the extraction device that is configured to be sized to accommodate at least part of the LCP therein once the LCP is extracted; and
  - an extractor member comprising:
    - a hollow needle that is configured to be extendable beyond the retrieval cavity; and
    - a deflectable probe that is configured to be extendable through the hollow needle and is further configured to cut through the ingrowth tissue that extends over the retrieval feature of the LCP in order to expose the retrieval feature of the LCP.

10. The extraction system of claim 9, wherein the hollow needle is fluidly coupled with a fluid source in order to inject a fluid in a space between the implanted LCP and the ingrowth tissue.

11. The extraction system of claim 10, wherein the deflectable probe comprises a preshaped cutting stylet.

12. The extraction system of claim 9, further comprising a retrieval loop that is configured to be extendable out from and beyond the retrieval cavity and is further configured to be manipulatable from the proximal region by an operator of the extraction system, wherein the retrieval loop is configured to be manipulatable by the operator to grasp the retrieval feature of the implanted LCP and pull the implanted LCP into the retrieval cavity.

13. An assembly for removing a chronically implanted Leadless Cardiac Pacemaker (LCP), the assembly comprising:
- a chronically implanted Leadless Cardiac Pacemaker (LCP) having a retrieval feature, wherein as a result of the LCP having been chronically implanted, there is ingrowth tissue extending over at least part of the retrieval feature;
- a garage that is configured to be sized to accommodate at least part of the LCP therein once the LCP is extracted; and
- a retrieval loop including a first control wire and a second control wire, the retrieval loop configured to selectively extend out of and beyond the garage by moving the first and/or second control wires, the retrieval loop comprising a first surface and an opposing second surface, wherein the first surface is configured to cut tissue better than the opposing second surface, and by moving the first and/or second control wires, cut away the ingrowth tissue to expose the retrieval feature of the LCP;
- wherein the retrieval loop is further configured to selectively grasp the exposed retrieval feature and pull the LCP at least partially into the garage by moving the first and/or second control wires.

14. The assembly of claim 13, wherein the retrieval loop forms at least part of a loop with the first surface on an inner side of the loop and the second surface on an outer side of the loop, wherein the first surface includes one or more cutting features and the second surface is free from cutting features.

15. The assembly of claim 14, wherein the first surface comprises an abrasive material and the second surface does not include the abrasive material.

16. The assembly of claim 14, wherein the first surface comprises a cutting edge and the second surface is free from a cutting edge.

17. The assembly of claim 14, wherein at least a portion of the first surface is electrically exposed to conduct applied RF energy to the ingrowth tissue to cut through the ingrowth tissue, and the second surface is not electrically exposed so as to insulate surrounding tissue from the applied RF energy.

* * * * *